US00PP24821P2

(12) United States Plant Patent
Van Noort

(10) Patent No.: US PP24,821 P2
(45) Date of Patent: Aug. 26, 2014

(54) *CIMICIFUGA* PLANT NAMED 'CHOCOHOLIC'

(50) Latin Name: *Cimicifuga ramosa*
Varietal Denomination: Chocoholic

(76) Inventor: Marco Van Noort, Warmond (NL)

( * ) Notice: Subject to any disclaimer, the term of this patent is extended or adjusted under 35 U.S.C. 154(b) by 289 days.

(21) Appl. No.: 12/799,158

(22) Filed: Apr. 20, 2010

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP9,988 P * 8/1997 McGourty ..... Plt./263.1
PP21,727 P2 * 2/2011 Oudolf ..... Plt./263.1

OTHER PUBLICATIONS

Anonymous. Perennial Results: Plant View—*Cimicifuga* Chocoholic PPAF available at http://www.perennialresource.com accessed Sep. 30, 2011.*

* cited by examiner

*Primary Examiner* — Wendy C Haas
(74) *Attorney, Agent, or Firm* — Penny J. Aguirre

(57) ABSTRACT

The new and distinct cultivar of ornamental plant of Black Snakeroot, *Cimicifuga* 'Chocoholic' with dark foliage of reddish purple, erect spikes of numerous, strongly-sweet, fragrant flowers with an overall dark purplish pink and white effect.

1 Drawing Sheet

Botanical classification: *Cimicifuga ramosa.*
Variety denomination: 'Chocoholic'.

BACKGROUND OF THE INVENTION

The present invention relates to the new and distinct cultivar of Black Snakeroot, botanically known as *Cimicifuga* 'Chocoholic', and hereinafter referred to as the cultivar 'Chocoholic' or the "new plant". The new plant was discovered by Marco van Noort in Warmond, The Netherlands in the summer of 2001 as a seedling of *Cimicifuga* 'Brunette' (not patented) from seed collected in fall 1999. The plant has been asexually propagated through division of the rhizome at the same nursery in Warmond, The Netherlands, and subsequent asexually propagated plants have been found to be identical to the original selection. 'Chocoholic' is in the Ranunculaceae family recognized as *Cimicifuga ramose*, but sometimes listed as *Cimicifuga racemosa, Cimicifuga simplex, Actaea ramosa, Actaea racemosa, Actaea simplex* and *Actaea cimicifuga.*

BRIEF SUMMARY OF THE PLANT

*Cimicifuga* 'Chocoholic' is unique from all other Black Snakeroot known to the inventor. Other forms have more green and less reddish-brown foliage and flowers with more white or lighter pink. The new plant has darker foliage than its female parent. The closest comparison variety is *Cimicifuga ramosa* 'Hillside Black Beauty' (U.S. Plant Pat. No. 9,988), which is different in that the new plant has dark greyed-purple foliage with more red tinting, and the flower buds of 'Chocoholic' are darker pink.

The following are traits of *Cimicifuga* 'Chocoholic' that in combination distinguish it from all other known Black Snakeroot known to the inventor:

1. Upright habit with moderately glossy foliage of reddish brown to reddish-purple.
2. Numerous strong, sweetly-fragrant flowers with dark greyed-red tepals and light creamy white tepals.
3. Flower buds with dark greyed-red sepals.

BRIEF DESCRIPTION OF ME DRAWINGS

The photographs of the new plant demonstrate the unique traits of the new plant and the overall appearance. The colors are as accurate as reasonably possible with color reproductions. Variation in ambient light spectrum, source and direction may cause the appearance of minor variation in color.

Figure 1:
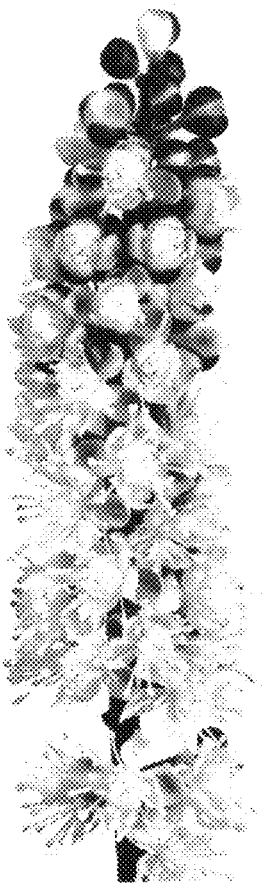
Figure 2:
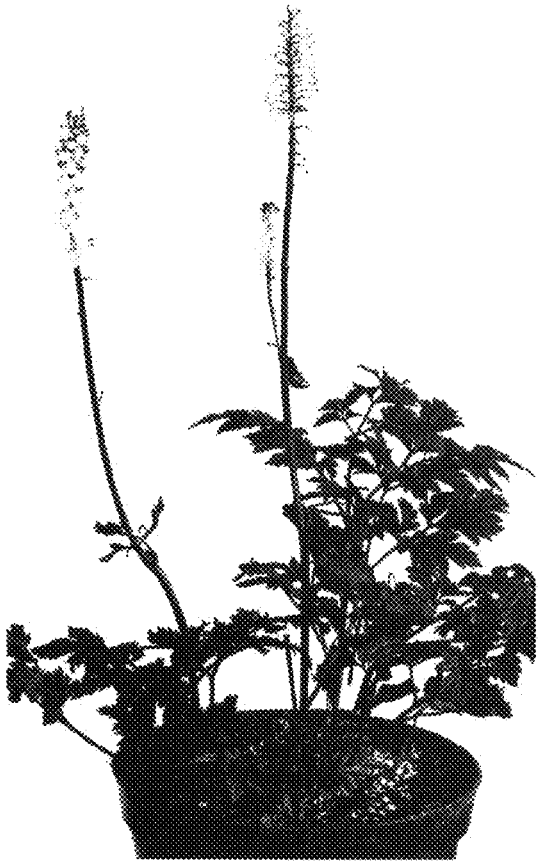
Figure 3:
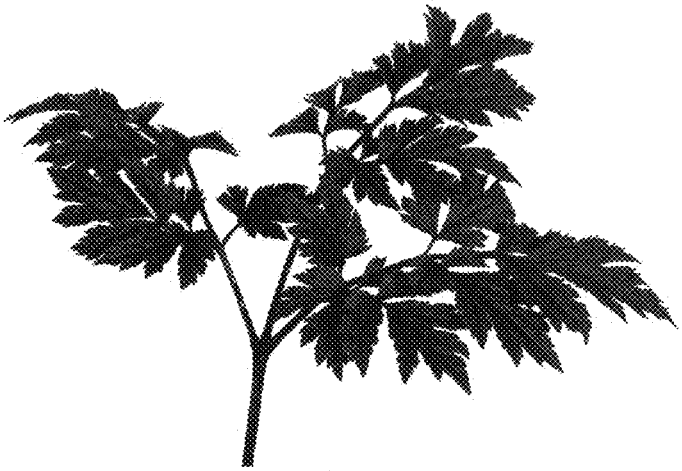

FIG. 1 shows a close-up of the flower.
FIG. 2 shows the plant in full flower.
FIG. 3 shows a close-up of the leaf.

DETAILED BOTANICAL DESCRIPTION

The following descriptions and color references are based on the 2007 edition of The Royal Horticultural Society Colour Chart except where common dictionary terms are used. *Cimicifuga* 'Chocoholic' has not been observed under all possible environments. The phenotype may vary slightly with different growing environments such as temperature, light, fertility, soil pH, moisture and plant maturity levels, but without any change in the genotype. The following observations and size descriptions are based on two-year old field grown plants in Warmond, the Netherlands with average day temperatures ranging between +10° C. and 25° C. and night temperatures between +3° C. to 14° C. Plants were not provided any additional light and no growth retardants were used.

Botanical classification: *Cimicifuga ramosa.*

Parentage: *Cimicifuga* 'Brunette' female parent (seed)×unknown *Cimicifuga* male parent (pollen).

Plant habit: Hardy herbaceous perennial; rhizomatous, upright, with inverted triangle shape when flowering; stems average 47.1 cm tall, plant width average 38.7 cm; main stems arising from base averaging two lateral branches per stem; flowering beginning September and continuing through October for about four to six weeks in Warmond, the Netherland.

Growth: Moderate vigor, spring rate 10 cm per month; time to finish to flower in 13 cm pots or larger is approximately 25 weeks.

Lateral branches: Average length 36.3 cm; average diameter 4.5 cm, internode length 8.1 cm;

Stem: Rounded, slightly glossy, glabrous, rigid and strong; color greyed-purple to brown between N186C and darker than 200A; pubescent with short hairs of about 0.1 mm; hair color nearest 155C.

Root: Thick, fleshy, not heavily branched; color dependent on soil type, usually light tan to cream.

Leaves: Alternate, palmately compound, dentate to coarsely biserrate, rugose, glabrous and moderately glossy above, minutely pubescent below; average 3 leaves per lateral branch; leaf size average 15.6 cm long and 19.1 cm wide; pubescent with short hairs of about 0.1 mm; hair color nearest 155C.

Leaflets: With acute apex, attenuate base; average 17 leaflets per leaf; average axillary leaflet 5.4 cm long and 3.4 cm wide; average terminal leaflet 6.7 cm long and 6.4 cm wide.

Leaf color: Young upper side between 144A and 146C, darker at margin nearest 200A; young underside 146C and margins darker 200B; mature leaves upper side between N186A and 203B with margins the same; mature leaves underside between 147A and slightly darker than 189A.

Veins: Pinnate, same color as leaf on adaxial and abaxial surfaces; color upper side between N186A and 203B; underside N186C.

Petiole: Average primary petiole 11.6 cm long and 3 mm diameter; secondary leaflet petiole average 4.1 cm long and 2 mm diameter; color upper side N186C with slight tinge of 200B; underside 200B.

Inflorescence: Raceme; average size 8.2 cm long excluding peduncle and 2.5 cm wide; average flowers per plant 160, average 50 per primary peduncle and 30 per secondary peduncle; flowering once per year in September through October with approximately 65% of flowers open at one time.

Buds three days prior to opening: Broadly obcordate average 4 mm long and 4 mm diameter, narrowly oblong, obtuse apex.

Bud color: Greyed-purple N187C to N187D before dehiscence.

Flower: Projected outward; actinomophic, rotate; average size 1.2 cm diameter and 1.0 cm deep; average longevity on the plant, one week; self-cleaning; strong sweet fragrance; flowers persist individually for 3 to 5 days whether on the plant or cut, self-cleaning; Calyx size; average 1.2 cm diameter and 6 mm long.

Tepals: Five, simple, entire, rotate arrangement, broadly elliptic with obtuse apex and fused at base, average size 5 mm long by 3 mm wide, two lower tepals caducous, three upper tepals persist about one week.

Teal color: Lower two tepals inside color begin greyed-red 182B with margins between NN155B and NN155C outside and dehisce shortly after opening; lower two tepals outside color between 187A and 1878B with white margins of NN155B to NN155C; upper three tepals begin between NN155B and NN155C on the inside and outside and remain between NN155B and NN155C upon full anthesis on both inside and outside.

Filaments: Average 40 in number, average 4 mm long and less than 0.4 mm diameter; color between NN155B and NN155C.

Another: Basifixed, broad oval to orbicular; average size 0.75 mm long and 0.4 mm across; color between NN155B and NN155C.

Pollen: Low quantity, globose, white 155D.

Style: Five; average 2.5 mm long and 0.2 mm diameter; between NN155C and NN155D; 4.0 mm by 0.25 mm, RHS 64A.

Stigma: Pointed, average 0.5 mm long; N155B.

Ovary: Globose, average 0.2 mm long and wide; between NN155C and NN155D.

Peduncle: Average length 19.1 cm of primary, 3.9 cm of secondary; average diameter of primary 3 mm and average diameter of secondary 2 mm; angle of primary peduncle vertical (0°), angle of secondary peduncle 20° down from vertical; brown between 200A and N200A; about 20 per plant; with short white pubescence of about 0.1 mm and 155C.

Pedicel: Average 5 mm long and 1 mm diameter; angle 85° from vertical, strong, greyed-purpose 187B to 187C; with minute pubescence of about 0.1 mm and 155C.

Fruit: No fruit or seed have yet been observed.

Hardiness, pest and disease resistance: The new plant grows best with ample moisture and adequate drainage, but is able to tolerate some drought when mature. Hardiness at least from USDA zone 4 through high temperatures of 35° C. Disease and pest resistance beyond what is typical of that of other Black Snakeroot has not been observed.

I claim:

1. A new and distinct cultivar of ornamental Black Snakeroot, *Cimicifuga* 'Chocoholic', as herein described and illustrated, with dark reddish purple foliage and strongly sweet fragrant reddish-purple flowers suitable as a potted plant, for the garden as an accent or en mass.

* * * * *